(12) United States Patent
Murakami

(10) Patent No.: US 7,595,155 B2
(45) Date of Patent: Sep. 29, 2009

(54) MULTIPLEX DETECTION PROBES

(75) Inventor: Taku Murakami, Irvine, CA (US)

(73) Assignees: Hitachi Chemical Research Center, Irvine, CA (US); Hitachi Chemical Co., Ltd., Tokyo (JP)

( * ) Notice: Subject to any disclaimer, the term of this patent is extended or adjusted under 35 U.S.C. 154(b) by 416 days.

(21) Appl. No.: 10/590,832

(22) PCT Filed: Feb. 28, 2005

(86) PCT No.: PCT/US2005/005955
§ 371 (c)(1), (2), (4) Date: Aug. 28, 2006

(87) PCT Pub. No.: WO2005/084210
PCT Pub. Date: Sep. 15, 2005

(65) Prior Publication Data
US 2007/0172827 A1   Jul. 26, 2007

Related U.S. Application Data

(60) Provisional application No. 60/548,635, filed on Feb. 27, 2004.

(51) Int. Cl.
C12Q 1/68 (2006.01)
G01N 33/53 (2006.01)
H01J 49/40 (2006.01)
C12N 15/11 (2006.01)
C07H 21/00 (2006.01)
C07H 21/04 (2006.01)

(52) U.S. Cl. .................. 435/6; 435/7.1; 250/287; 536/23.1; 536/24.3

(58) Field of Classification Search .......... None
See application file for complete search history.

(56) References Cited

U.S. PATENT DOCUMENTS 5,595,875 A   1/1997   Law et al.
6,635,452 B1  10/2003  Monforte et al.

FOREIGN PATENT DOCUMENTS

WO   WO 99/60007   11/1999
WO   WO 03/003015  1/2003

OTHER PUBLICATIONS

PCT/US05/05955 Search Report and Written Opinion, Aug. 30, 2005.
Rule, G. S., et al., "Characteristics of DNA-tagged liposomes allowing their use in capillary-migration, sandwich-hybridization assays," *Analytical Biochemistry*, vol. 244, No. 2, 1997, pp. 260-269.
Alfonta, L., et al., "Liposomes labeled with biotin and horseradish peroxidase: a probe for the enhanced amplification of antigen-antibody or oligonucleotide-DNA sensing processes by the precipitation of an insoluble product on electrodes," *Analytical Chemistry*, vol. 73, No. 1, Jan. 2001, pp. 91-102.
Lund, V., et al., "Assessment of methods for covalent binding of nucleic acids to magnetic beads, Dynabeads™, and the characteristics of the bound nucleic acids in hybridization reactions," *Nucleic Acids Research*, vol. 16, No. 22, 1988.
Deng, W.-G., et al., "Quantitative analysis of binding of transcription factor complex to biotinylated DNA probe by a streptavidin-agarose pulldown assay," *Analytical Biochemistry*, vol. 323, No. 1, Dec. 2003, pp. 12-18.
Stears, R. L., et al., "A novel, sensitive detection system for high-density microarrays using dendrimer technology," *Physiological Genomics*, vol. 3, Sep. 2000, pp. 93-99.
Dunbar, S. A., et al., "Quantitative multiplexed detection of bacterial pathogens: DNA and protein applications of the Luminex LabMAP system," *Journal of Microbiological Methods*, vol. 53, May 2003, pp. 245-252.

*Primary Examiner*—James Martinell
(74) *Attorney, Agent, or Firm*—Knobbe, Martens, Olson & Bear LLC

(57) ABSTRACT

The present invention comprises detection probes utilizing vesicles or soluble bodies to retain multiple mass tag molecules. The detection probes may be used to simultaneously assay a plurality of different biological samples, each comprising a plurality of analytes, by immobilizing the analytes from each of the samples on a surface incubating the surface with a set of the detection probes, each having mass tag molecules with different masses, removing the unbound detection probe, collecting the first and second mass tag molecules from the bound detection probe, and quantifying the first and second mass tag molecules collected.

43 Claims, 8 Drawing Sheets

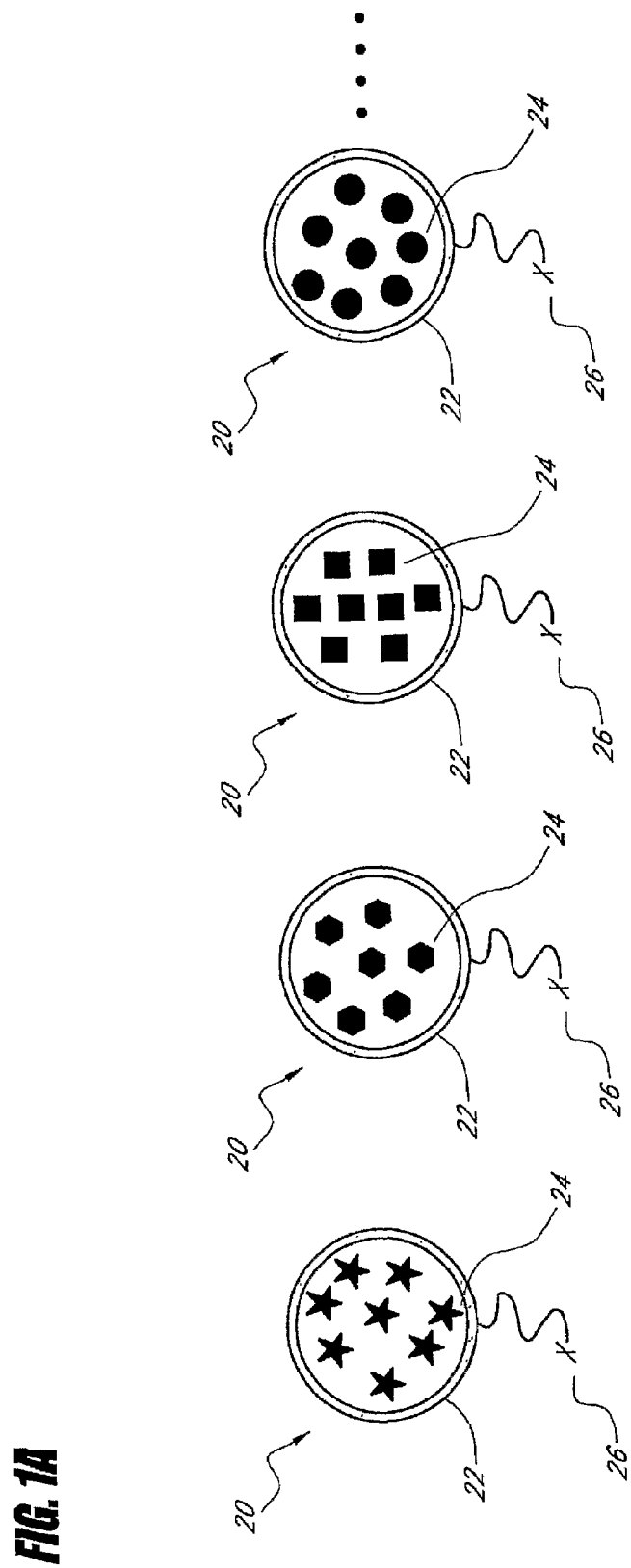

MULTIPLEX DETECTION PROBES

RELATED APPLICATION

The present application is a non-provisional application claiming priority to U.S. Provisional Application No. 60/548,635, filed 27 Feb. 2004.

BACKGROUND OF THE INVENTION

1. Field of the Invention

The present invention relates generally to the field of chemical analysis. More particularly, it concerns tag reagents for sensitive, high throughput detection and analysis of target molecules.

2. Description of the Related Art

Chemical labels, otherwise known as tags or signal groups, are widely used in chemical analysis. Among the types of molecules used are radioactive atoms, fluorescent reagents, luminescent reagents, metal-containing compounds, electron-absorbing substances and light absorbing compounds. A number of different types of molecules have been used as tags that can be differentiated under mass spectrometry. Chemical signal groups can be combined with reactivity groups so that they might be covalently attached to the target, the substance being detected.

However, current detection probes do not adequately allow highly multiplex detection and analysis of molecules. Microarrays can analyze the expression profiles of thousands of genes, but researchers can typically handle only one or two samples on a single microarray chip or slide because their fluorescent or luminescent detection systems have very limited multiplex capability. In addition to the added costs caused by the necessary use of multiple chips or slides, the limited analytical capacity of existing methods makes it difficult to replicate microarray experiments and/or compare data among samples. Moreover, while many other applications and assays have been developed using microplate formats, the use of current multiplex methods and devices limit the number of the samples that can be used in each well. Using current methods and devices of multiplex analysis of molecules requires multiple wells and/or plates for higher throughput and reproducible data.

SUMMARY OF THE INVENTION

Embodiments of the present invention provide compositions and methods relating to the use of release tag compounds for detection and analysis of target molecules, which increase signal intensity of molecular probes and allows for sensitive, high-throughput multiplex analysis. Liposome embodiments preferably contain a plurality of mass tag molecules, ranging in number from 1 to $2 \times 10^8$, which provides stronger signaling and allows for highly sensitive multiplex analysis of molecules. Other embodiments can contain many orders of magnitude more mass tag molecules. For example, a solid particle having a diameter of 0.5 μm can contain up to $2 \times 10^{10}$ mass tag molecules. Still other embodiments can contain even more mass tag molecules, depending the size of the embodiments and the density of the mass tag molecules, but ordinarily there are less than $1 \times 10^{20}$, and more preferably less than $1 \times 10^{15}$ molecules.

Preferred embodiments comprise detection probes utilizing vesicles to retain multiple mass tag molecules, which are molecules with a specific molecular mass (or mobility) detectable by mass spectrometry, electrophoresis, chromatography or other analytical methods known to those skilled in the art. As used herein, a "vesicle" may include molecules encapsulated within the vesicle. Embodiments include, but are not limited to, encapsulation vesicles, uni-lamellar vesicles, and multi-lamellar vesicles. The various vesicles preferably comprise liposomes, which preferably comprise a plurality of phospholipids. In certain embodiments, the mass tag molecules can be attached to the phospholipids themselves. Other molecules, such as cholesterol or other hydrophobic molecules, also can be entrapped in the lipid bilayer through hydrophobic interaction as mass tag molecules.

Further embodiments of the present invention comprise various carriers of mass tag molecules, including, but not limited to: emulsions, soluble beads, soluble capsules, and soluble porous beads.

Embodiments of the present invention can be used with various analytical methods and systems, including, but not limited to: hybridization assays, multiplex microarray assays, multiplex immunoassays, multiplex hybridization assays, multiplex CpG methylation assays, capillary assays, mass spectrometry, electrophoresis, and other analytical methods and systems known to those skilled in the art.

One embodiment of the present invention is a detection probe comprising an external vesicle comprising a plurality of amphiphilic molecules forming a vesicle membrane; a plurality of mass tag molecules encapsulated within the vesicle, within the vesicle membrane or adsorbed on the vesicle membrane; and a probe attached to the vesicle. In further embodiments, the external vesicle is easily disrupted to release the mass tag molecules, the plurality of mass tag molecules comprise at least a part of the vesicle membrane. Further embodiments additionally comprise at least one vesicle encapsulated within the external vesicle, at least a part of the external and encapsulated vesicles comprising the mass tag molecules, and in a further embodiment thereof, the external and encapsulated vesicles are easily disrupted to release the mass tag molecule. In further embodiments, the external vesicle is a liposome, a polymersome, or an emulsion such as an oil-in-water (O/W) emulsion, water-in-oil-in-water (W/O/W) emulsion or solid-in-oil-in-water (S/O/W) emulsion. In a further embodiment, the probe comprises at least one molecule selected from the group consisting of chemical residues, polynucleotides, polypeptides, and carbohydrates, and the molecule may be immobilized. In further embodiments, the mass tag molecules are a biopolymer such as a polynucleotide, polypeptide or polysaccharide; a synthetic polymer such as a block copolymer; amphiphilic molecules bound to a biopolymer such as a polynucleotide, polypeptide, polysaccharide or a synthetic polymer such as a block copolymer.

Another embodiment of the invention is a detection probe, comprising a body comprising a material that can become soluble upon physical or chemical stimulation and at least one mass tag molecule, and a probe attached to the body. In further embodiments, the body may comprise a soluble bead which may be porous, or a soluble capsule. In further embodiments, the probe comprises at least one molecule selected from the group consisting of chemical residues, polynucleotides, polypeptides, and carbohydrates, and the molecule may be immobilized. In further embodiments, the mass tag molecule may be a biopolymer or a synthetic polymer.

Another embodiment of the present invention is a set of detection probes comprising: a first detection probe comprising a first body comprising a material that can become soluble upon physical or chemical stimulation and at least one first mass tag molecule, and a first probe attached to the first body; and a second detection probe comprising a second body comprising a material that can become soluble upon physical or chemical stimulation and at least one second mass tag molecule, and a second probe attached to the second body; wherein the mass of the first mass tag molecule is different from the mass of the second mass tag molecule. In further embodiments, the first and second bodies comprise soluble beads, which may be porous, or soluble capsules. In further embodiments, the first and second probes comprise at least one molecule selected from the group consisting of chemical residues, polynucleotides, polypeptides, and carbohydrates, and the molecule may be immobilized. In further embodiments, the first and second mass tag molecules are biopolymers, such as polynucleotides, polypeptides or polysaccharides, synthetic polymers, such as block copolymers, amphiphilic molecules bound to a biopolymer or synthetic polymer, or amphiphilic molecules bound to a polynucleotide, polypeptide, polysaccharide or block copolymer.

Another embodiment of the present invention is a method of simultaneously assaying a plurality of different biological samples, each of said samples comprising a plurality of analytes, the method comprising: immobilizing said analytes from each of said samples on a surface; incubating said surface with the set of detection probes described above; removing unbound detection probe; collecting the first and second mass tag molecules from the bound detection probe; and quantifying the first and second mass tag molecules collected. In further embodiments, the binding of the first and second detection probe results from the binding of molecules such as DNA, RNA, aptamers, proteins, peptides, polysaccharides, chemical residues on a biological molecule, or a small chemical molecule, or from the binding of complementary nucleotide sequences, antigen-antibody binding, protein-protein binding, or the binding of a chemical residue and a biological molecule. In further embodiments, the mass tag molecules are collected after stimulation of the first and second detection probes by a solvent change, chemical addition, pH change, agitation, sonication, heating, laser irradiation, light irradiation or freeze-thaw process. In a further embodiment the mass tag molecules may be quantified by mass spectrometry, electrophoresis or chromatography.

Another embodiment of the present invention is a method of analyzing a plurality of different biological samples, each of said samples comprising a plurality of analytes, said method comprising: labeling each sample with a detection probe comprising a body comprising a material that can become soluble upon physical or chemical stimulation and at least one mass tag molecule, and a probe attached to the body, wherein the mass tag molecule of the detection probe labeling each sample has a different mass; incubating the labeled sample with an immobilized target molecule capable of specifically binding to one of said analytes; removing unbound labeled sample; collecting the mass tag molecules from the bound probe; and quantifying the mass tag molecules collected. In further embodiments, the binding of the detection probe results from the binding of molecules such as DNA, RNA, aptamers, proteins, peptides, polysaccharides, chemical residues on biological molecules, or small chemical molecules, or from the binding of complementary nucleotide sequences, antigen-antibody binding, protein-protein binding, or binding of a chemical residue and a biological molecule. In further embodiments, the mass tag molecules are collected after stimulation of the detection probes.

Another embodiment of the present invention is set of detection probes comprising: a first detection probe comprising a first external vesicle comprising a plurality of amphiphilic molecules forming a first vesicle membrane, a plurality of first mass tag molecules encapsulated within the first external vesicle, within the first vesicle membrane or adsorbed on the first vesicle membrane, and a probe attached to the first external vesicle; and a second detection probe comprising a second external vesicle comprising a plurality of amphiphilic molecules forming a second vesicle membrane, a plurality of second mass tag molecules encapsulated within the second external vesicle, within the second vesicle membrane or adsorbed on the second vesicle membrane, and a probe attached to the second external vesicle; wherein the mass of the first mass tag molecules is different from the mass of the second mass tag molecules. In further embodiments, the first and second external vesicles are easily disrupted to release the mass tag molecules. In further embodiments, each of the first and second mass tag molecules is encapsulated within each of the first and second external vesicles, or within each of the first and second vesicle membranes, or is adsorbed on each of the first and second vesicle membranes, respectively. In further embodiments, the mass tag molecules comprise at least a part of the vesicle membranes. In further embodiments, each of the first and second external vesicles further comprise at least one encapsulated vesicle, at least a part of the external and encapsulated vesicles comprising the mass tag molecule, and the external and encapsulated vesicles may be easily disrupted to release the mass tag molecules. In further embodiments, the external vesicles are liposomes, polymerosomes, or emulsions such as oil-in-water (O/W) emulsions, water-in-oil-in-water (W/O/W) emulsions or solid-in-oil-in-water (S/O/W) emulsions. In further embodiments, the probes each comprise at least one molecule selected from the group consisting of chemical residues, polynucleotides, polypeptides, and carbohydrates, and the molecule may be immobilized. In further embodiments, the first and second mass tag molecules may be biopolymers such as polynucleotides, polypeptides or polysaccharides, synthetic polymers such as block copolymers, amphiphilic molecules bound to a biopolymer such as a a polynucleotide, polypeptide, or polysaccharide, or a synthetic polymer such as a block copolymer.

Another embodiment of the present invention is a method of simultaneously assaying a plurality of different biological samples, each of said samples comprising a plurality of analytes, said method comprising: immobilizing said analytes from each of said samples on a surface; incubating said surface with a set of detection probes comprising: a first detection probe comprising a first external vesicle comprising a plurality of amphiphilic molecules forming a first vesicle membrane, a plurality of first mass tag molecules encapsulated within the first external vesicle, within the first vesicle membrane or adsorbed on the first vesicle membrane, and a probe attached to the first external vesicle; and a second detection probe comprising a second external vesicle comprising a plurality of amphiphilic molecules forming a second vesicle membrane, a plurality of second mass tag molecules encapsulated within the second external vesicle, within the second vesicle membrane or adsorbed on the second vesicle membrane, and a probe attached to the second external vesicle; wherein the mass of the first mass tag molecules is different from the mass of the second mass tag molecules; removing unbound detection probe; collecting the first and second mass tag molecules from the bound detection probe; and quantifying the first and second mass tag molecules collected. In further embodiments, the binding of the detection probe results from the binding of molecules such as DNA, RNA, aptamers, proteins, peptides, polysaccharides, chemical residues on biological molecules, or small chemical molecules, or from the binding of complementary nucleotide sequences, antigen-antibody binding, protein-protein binding, or binding of chemical residues and biological molecules. In further embodiments, the mass tag molecules are collected after stimulation of the detection probes by a solvent change, chemical addition, pH change, agitation, sonication, heating, laser irradiation, light irradiation or freeze-thaw process. In further embodiments, the mass tag molecules are quantified by mass spectrometry, electrophoresis or chromatography.

Another embodiment of the present invention is a method of analyzing a plurality of different biological samples, each of said samples comprising a plurality of analytes, said method comprising: labeling each sample with a detection probe comprising an external vesicle comprising a plurality of amphiphilic molecules forming a vesicle membrane, a plurality of mass tag molecules encapsulated within the vesicle, within the vesicle membrane or adsorbed on the vesicle membrane, and a probe attached to the vesicle, wherein the mass tag molecules of the detection probe labeling each sample have a different mass; incubating the labeled sample with an immobilized target molecule capable of specifically binding to one of said analytes; removing unbound labeled sample; collecting the mass tag molecules from the bound probe; and quantifying the mass tag molecules collected. In further embodiments, the binding of the detection probe results from the binding of molecules such as DNA, RNA, aptamers, proteins, peptides, polysaccharides, chemical residues on biological molecules, or small chemical molecules, or the binding of complementary nucleotide sequences, antigen-antibody binding, protein-protein binding, or the binding of chemical residues and biological molecules. In further embodiments, the mass tag molecules are collected after stimulation of the detection probes by a solvent change, chemical addition, pH change, agitation, sonication, heating, laser irradiation, light irradiation or freeze-thaw process. In further embodiments, the mass tag molecules are quantified by mass spectrometry, electrophoresis or chromatography.

Another embodiment of the present invention is a method of simultaneously assaying a plurality of different biological samples, each of said samples comprising a plurality of analytes, said method comprising: immobilizing said analytes from each of said samples on a surface; incubating said surface with a set of detection probes comprising: a first detection probe comprising a first external vesicle comprising a plurality of first mass tag molecules forming a first vesicle membrane, and a probe attached to the first external vesicle; and a second detection probe comprising a second external vesicle comprising a plurality of second mass tag molecules forming a second vesicle membrane, and a probe attached to the second external vesicle; removing unbound detection probe; collecting the first and second mass tag molecules from the bound detection probe; and quantifying the first and second mass tag molecules collected. In further embodiments, the binding of the detection probe results from the binding of molecules such as DNA, RNA, aptamers, proteins, peptides, polysaccharides, chemical residues on biological molecules, or small chemical molecules, or the binding of complementary nucleotide sequences, antigen-antibody binding, protein-protein binding, or the binding of chemical residues and biological molecules. In further embodiments, the mass tag molecules are collected after stimulation of the detection probes by a solvent change, chemical addition, pH change, agitation, sonication, heating, laser irradiation, light irradiation or freeze-thaw process. In further embodiments, the mass tag molecules are quantified by mass spectrometry, electrophoresis or chromatography.

Another embodiment of the present invention is a method of analyzing a plurality of different biological samples, each of said samples comprising a plurality of analytes, said method comprising: labeling each sample with a detection probe comprising an external vesicle comprising a plurality of mass tag molecules forming a vesicle membrane and a probe attached to the vesicle, wherein the mass tag molecules of the detection probe labeling each sample have a different mass; incubating the labeled sample with an immobilized target molecule capable of specifically binding to one of said analytes; removing unbound labeled sample; collecting the mass tag molecules from the bound probe; and quantifying the mass tag molecules collected. In further embodiments, the binding of the detection probe results from the binding of molecules such as DNA, RNA, aptamers, proteins, peptides, polysaccharides, chemical residues on biological molecules, or small chemical molecules, or from the binding of complementary nucleotide sequences, antigen-antibody binding, protein-protein binding, or the binding of chemical residues and biological molecules. In further embodiments, the mass tag molecules are collected after stimulation of the detection probes by a solvent change, chemical addition, pH change, agitation, sonication, heating, laser irradiation, light irradiation or freeze-thaw process. In further embodiments, the mass tag molecules are quantified by mass spectrometry, electrophoresis or chromatography.

BRIEF DESCRIPTION OF THE DRAWINGS

FIGS. 1A-1C are schematic representations of various types of mass tag-containing vesicles.

DETAILED DESCRIPTION OF THE PREFERRED EMBODIMENT

Figure 1B:
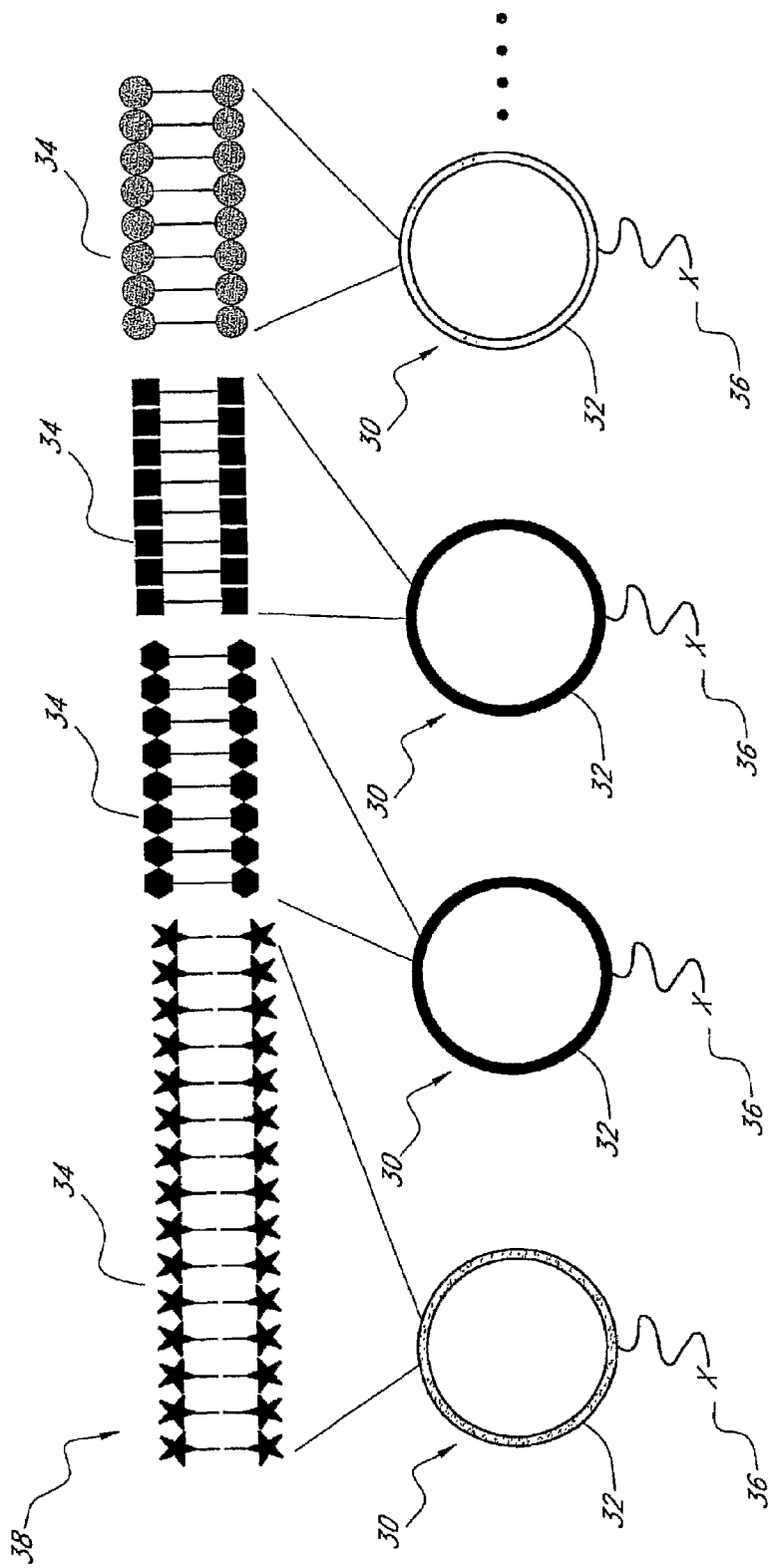

Embodiments of the present invention comprise detection probes utilizing various forms of vesicles to retain multiple mass tag molecules. Mass tag molecules are disclosed in U.S. Pat. No. 6,635,452, which is hereby incorporated in its entirety by reference. Mass tag molecules may also be referred to as labels or signals. Examples of the types of mass tag molecules used in the present invention include a repertoire of compounds, preferably ones that share similar mass spectrometric desorption properties and have similar or identical coupling chemistries in order to streamline synthesis of multiple mass label variants. A mass tag molecule of the present invention is detectable by mass spectrometry. Representative types of mass spectrometric techniques include matrix-assisted laser desorption ionization, direct laser-desorption, electrospray ionization, secondary neutral, and secondary ion mass spectrometry, with laser-desorption ionization being preferred. The dynamic range of mass spectral measurements can generally be extended by use of a logarithmic amplifier and/or variable attenuation in the processing and analysis of the signal.

Mass tag molecules may include a vast array of different types of compounds including biopolymers and synthetic polymers. Representative biological monomer units that may be used as mass tag molecules, either singly or in polymeric form, include amino acids, nonnatural amino acids, nucleic acids, saccharides, carbohydrates, peptide mimics and nucleic acid mimics. Preferred amino acids include those with simple aliphatic side chains (e.g., glycine, alanine, valine, leucine and isoleucine), amino acids with aromatic side chains (e.g., phenylalanine, tryptophan, tyrosine, and histidine), amino acids with oxygen and sulfur containing side chains (e.g., serine, threonine, methionine and cysteine), amino acids with side chains containing carboxylic or amide groups (e.g., aspartic acid, glutamic acid, asparagine and glutamine), and amino acids with side chains containing strongly basic groups (e.g., lysine and arginine), and proline. Derivatives of the above described amino acids are also contemplated as monomer units. An amino acid derivative as used herein is any compound that contains within its structure the basic amino acid core of an amino-substituted carboxylic acid, with representative examples including but not limited to azaserine, fluoroalanine, GABA, ornithine, norleucine and cycloserine. Peptides derived from the above described amino acids can also be used as monomer units. Representative examples include both naturally occurring and synthetic peptides with molecular weight above about 500 Daltons, with peptides from about 500-5000 Daltons being preferred. Representative examples of saccharides include ribose, arabinose, xylose, glucose, galactose and other sugar derivatives composed of chains from 2-7 carbons. Representative polysaccharides include combinations of the saccharide units listed above linked via a glycosidic bond. The sequence of the polymeric units within any one mass tag molecule is not critical; the total mass is the key feature of the tag molecules.

The monomer units according to the present invention also may be composed of nucleobase compounds. As used herein, the term nucleobase refers to any moiety that includes within its structure a purine, a pyrimidine, a nucleic acid, nucleoside, nucleotide or derivative of any of these, such as a protected nucleobase, purine analog, pyrimidine analog, folinic acid analog, methyl phosphonate derivatives, phosphotriester derivatives, borano phosphate derivatives or phosphorothioate derivatives.

Mass tag molecules according to the present invention may also include any organic or inorganic polymer that has a defined mass value, remains water soluble during bioassays and is detectable by mass spectrometry. Representative synthetic monomer units that may be used as mass units in polymeric form include polyethylene glycols, polyvinyl phenols, polymethyl methacrylates, polypropylene glycol, polypyroles, and derivatives thereof. A wide variety of polymers would be readily available to one of skill in the art based on references such as Allcock (Contemporary Polymer Chemistry, Prentice-Hall, Inc., Englewood Cliffs, N.J., 1981), which describes the properties of many additional polymers contemplated for use in the present invention. The polymers may be composed of a single type of monomer unit or combinations of monomer units to create a mixed polymer. The sequence of the polymeric units within any one mass tag molecule is not critical; the total mass is the key feature of the tag molecule.

For nonvolatile mass tag molecules having a mass below about 500 Da, usually significant ionic character is required; representative examples include polyethylene glycol oligomers of quaternary ammonium salts (e.g., R—(O—$CH_2$—$CH_2$)$_n$—$N(CH_3)_3{}^+Cl^-$) and polyethylene glycol oligomers of carboxylic acids and salts (e.g., R—(O—$CH_2$—$CH_2$)$_n$—$CO_2$—$Na^+$).

Examples of involatile mass tag molecules typically include small oligomers of polyethylene glycol and small peptides (natural or modified) less than about 500 Da in molecular weight. In these instances, as for all of the cases considered herein, mass analysis is not by electron attachment.

Mass tag molecules of the present invention may also include a variety of nonvolatile and involatile organic compounds which are nonpolymeric. Representative examples of nonvolatile organic compounds include heme groups, dyes, organometallic compounds, steroids, fullerenes, retinoids, carotenoids and polyaromatic hydrocarbons.

Mass tag molecules of the present invention comprise molecules with a specific molecular mass or mobility detectable by various analytical methods and systems including, but not limited to: hybridization assays, multiplex microarray assays, multiplex immunoassays, multiplex hybridization assays, multiplex CpG methylation assays, capillary assays, mass spectrometry, electrophoresis, and other analytical methods known to those skilled in the art.

The embodiment illustrated in FIG. 1A shows a number of detection probes 20 comprising an encapsulation vesicle 22 having at least one mass tag molecule 24 preferably located within the vesicle 22. The vesicle preferably comprises at least one interaction site 26 on its surface. In each probe, the vesicle encapsulates at least one mass tag molecule 24 with a specific molecular mass.

The embodiment illustrated in FIG. 1B shows a detection probe 30 comprising a uni-lamellar vesicle 32. The membrane 38 of the vesicle 32 preferably comprises mass tag molecules 34 with a specific molecular mass. Further embodiments of the uni-lamellar vesicles 32 comprise at least one mass tag molecule 34 preferably located within the uni-lamellar vesicle 32. The mass tags 34 located within the vesicle 32 are preferably the same type of mass tags 34 as those comprising the membrane 38. The vesicle preferably comprises at least one interaction site 36 on its surface.

Figure 1C:
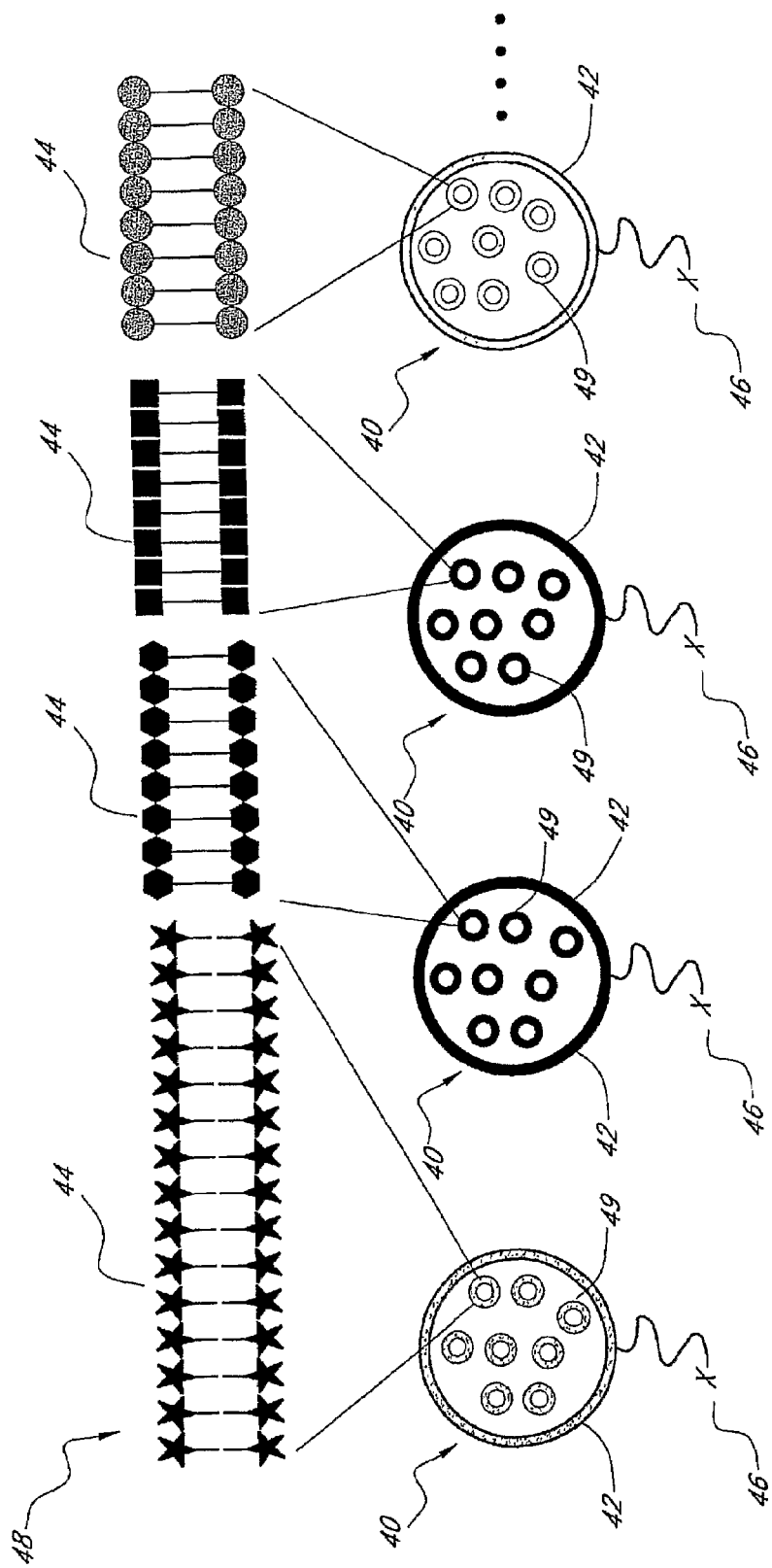

FIG. 1C shows another preferred embodiment of the present invention which comprises a detection probe 40, further comprising a multi-lamellar vesicle 42. The membrane 48 of the vesicle preferably comprises mass tag molecules 44 with a specific molecular mass. Further embodiments of the multi-lamellar vesicles 42 comprise at least one mass tag molecule 44 preferably located within the multi-lamellar vesicle 42. The vesicle 42 preferably encapsulates at least one smaller vesicle 49 which preferably contains the same type of mass tags 44 as those comprising the membrane 48. The mass tags 44 located within the vesicle 42 are preferably the same type of mass tags 44 as those comprising the membrane 48. The vesicle 42 preferably comprises at least one interaction site 46 on its surface.

Embodiments of the detection probes 20, 30, and 40 of FIGS. 1A-1C utilize vesicles comprising liposomes, which can carry and release mass tag molecules. In order to release the mass tag molecules for detection, these carriers are preferably easily disrupted by physical stimulation, including but not limited to: heat, centrifugation, laser irradiation, sonication, electricity, evaporation, freeze-thaw process, or other methods known to those skilled in the art. Disruption may also be preferably achieved by chemical stimulation including, but not limited to: addition of organic solvent, detergent, acid, alkaline, enzyme, chaotropic reagents (urea, guanidium chloride, etc.), change of buffer, change of salt, change of concentration, change of pH, change of osmotic pressure, and other methods known to those skilled in the art.

In preferred embodiments, the probes 20, 30, and 40 have interaction sites 26, 36, and 46 on their outer surface comprising chemical residues, polynucleotides, proteins, peptides, carbohydrate or other small compounds known to those skilled of the art. In preferred embodiments, the molecules of the interaction sites 26, 36, and 46 are immobilized. The interaction sites 26, 36, and 46 of the probes 20, 30, and 40 can preferably be used to analyze various intermolecular interactions such as nucleotide-nucleotide interactions (hybridization), antigen-antibody interactions (immunoassay), protein-protein interactions, small compound-protein interactions, small compound-cell interactions, and other interactions known to those skilled in the art.

As defined herein, the term "interaction site" refers to a group capable of reacting with the molecule whose presence is to be detected. For example, the interaction site may be a biomolecule capable of specific molecular recognition. Biomolecules capable of specific molecular recognition may typically be any molecule capable of specific binding interactions with unique molecules or classes of molecules, such as peptides, proteins, polynucleic acids, carbohydrate, and other chemical molecules, etc.

Thus, interaction sites disclosed herein for use with the disclosed methods encompass polypeptides and polynucleic acids. As used herein, polypeptides refer to molecules containing more than one amino acid (which include native and non-native amino acid monomers). Thus, polypeptides includes peptides comprising 2 or more amino acids; native proteins; enzymes; gene products; antibodies; protein conjugates; mutant or polymorphic polypeptides; post-translationally modified proteins; genetically engineered gene products including products of chemical synthesis, in vitro translation, cell-based expression systems, including fast evolution systems involving vector shuffling, random or directed mutagenesis, and peptide sequence randomization. In preferred embodiments polypeptides may be oligopeptides, antibodies, enzymes, receptors, regulatory proteins, nucleic acid-binding proteins, honnones, or protein product of a display method, such as a phage display method or a bacterial display method. More preferred polypeptide interaction sites are antibodies and enzymes. As used herein, the phrase "product of a display method" refers to any polypeptide resulting from the performance of a display method which are well known in the art. It is contemplated that any display method known in the art may be used to produce the polypeptides for use in conjunction with the present invention.

Similarly, "polynucleic acids" refer to molecules containing more than one nucleic acid. Polynucleic acids include lengths of 2 or more nucleotide monomers and encompass nucleic acids, oligonucleotides, oligos, polynucleotides, DNA, genomic DNA, mitochondrial DNA (mtDNA), copy DNA (cDNA), bacterial DNA, viral DNA, viral RNA, RNA, message RNA (mRNA), transfer RNA (tRNA), ribosomal RNA (rRNA), catalytic RNA, clones, plasmids, M13, P1, cosmid, bacteria artificial chromosome (BAC), yeast artificial chromosome (YAC), amplified nucleic acid, amplicon, PCR product and other types of amplified nucleic acid. In preferred embodiments, the polynucleic acid may be an oligonucleotide.

Additional embodiments of detection probes of the present invention include emulsions. Particularly preferred embodiments comprise oil/water (O/W) emulsions, water/oil/water (W/O/W) emulsions, and solid/oil/water (S/O/W) emulsions, which comprise vesicles with interaction sites on their outer surfaces. The mass tag molecules are preferably encapsulated in the vesicles. In alternative embodiments, the detergents, which comprise the interface between oil and water or oil and solid phases, works as a mass tag.

Additional embodiments of detection probes of the present invention include soluble bead probes, which comprise beads with interaction sites on their outer surface. The beads preferably comprise a material that can become soluble upon physical or chemical stimulation. The mass tag molecules are preferably solidified with the material. In alternative embodiments, the bead material can preferably work as a mass tag.

Further embodiments of detection probes comprise soluble capsules comprising interaction sites on their surface. The capsules preferably comprise a material that becomes soluble upon physical or chemical stimulation. In order to release the mass tag molecules for detection, these carriers are preferably easily disrupted by physical stimulation, including but not limited to: heat, centrifugation, laser irradiation, sonication, electricity, evaporation, freeze-thaw process, or other methods known to those skilled in the art. Disruption may also be preferably achieved by chemical stimulation including, but not limited to: addition of organic solvent, detergent, acid, alkaline, enzyme, chaotropic reagents (urea, guanidium chloride, etc.), change of buffer, change of salt, change of concentration, change of pH, change of osmotic pressure, and other methods known to those skilled in the art. The mass tag molecules are preferably encapsulated within the soluble capsule. In alternative embodiments, the bead material can preferably work as a mass tag.

Additional embodiments of detection probes of the present invention include soluble porous bead probes, which comprise beads with interaction sites on their outer surface. The beads preferably comprise multiple probes, which can preferably be filled or covered with a material that can become soluble upon physical or chemical stimulation. The mass tag molecules are preferably incorporated into the pores. In alternative embodiments, the bead material can preferably work as a mass tag.

The soluble bead probes, soluble capsule probes, and soluble porous bead probes preferably utilize a material that changes its solubility or shape upon physical (heat, centrifugation, laser irradiation, sonication, electricity, evaporation, freeze-thaw process, etc.) or chemical stimulation (addition of organic solvent, detergent, acid, alkaline, enzyme, chaotropic reagent (urea, guanidium chloride, etc.), change of buffer/salt concentration, pH, osmotic pressure, etc.). These materials work as "mass tags", or "mass tags" can be solidified, polymerized or encapsulated with them.

For example, beads or capsules made of nucleotides, peptides, saccharides or polymers can preferably become soluble by degrading these components by enzymatic or chemical reactions, or can be deformed by other means of physical or chemical stimulation. Probes made of sol-gel material (collagen, agarose, pectin, etc.) are also preferably deformed through sol-gel transformation upon heating, pH change or other forms of stimulation known to those skilled in the art. Dendrimer, sugar balls, or other forms of drug delivery carriers can also be preferably utilized for multiplex probes as such materials can typically release incorporated mass tag molecules upon stimulation.

The use of mass tag molecules in various embodiments of the present invention allows highly multiplexed assays because the mass tag molecules can be identified by their molecular mass and various analytical methods as mentioned above. Analytical methods, including but not limited to mass spectrometry, can detect even one-mass differences. For example, sixty-three fluorescent dyes of Table 1 (below) and twenty-two phospholipids of Table 2 (below) have at least five mass differences between each other, so they can be identified and quantified by mass spectrometry simultaneously.

TABLE 1

Fluorescent Dyes (cited from Synthegen Catalog)

| Chemical Name | M.W. | Catalog Number |
|---|---|---|
| 7-methoxycoumarin-3-carboxylic acid | 202.0 | 1307 |
| Pacific Blue | 224.2 | 1304 |
| 7-diethylaminocoumarin-3-carboxylic acid | 243.0 | 1306 |
| Marina Blue | 252.3 | 1303 |
| NBD-X | 276.3 | 1720 |
| Alexa Fluor 350 | 295.4 | 1730 |
| BODIPY 493/503 | 302.0 | 1117 |
| EDANS | 307.1 | 1500 |
| BODIPY R6G | 322.0 | 1106 |
| AMCA-X (Coumarin) | 328.0 | 1300 |
| BODIPY 564/570 | 348.0 | 1108 |
| 5-Carboxyfluorescein (FAM) | 358.0 | 1001 |
| BODIPY 581/591 | 374.0 | 1109 |
| BODIPY FL-X | 387.0 | 1104 |
| Rhodamine Green-X | 394.0 | 1305 |
| 6-Carboxytetramethylrhodamine (TAMRA) | 413.0 | 1202 |
| Oregon Green 500 | 431.0 | 1102 |
| MAX | 441.0 | 1118 |
| Cascade Yellow | 448.5 | 1706 |
| Carboxynapthofluorescein | 458.5 | 1725 |
| PyMPO | 467.4 | 1710 |
| JOE | 487.0 | 1009 |
| Oregon Green 514 | 494.0 | 1103 |
| Cy3 | 508.6 | 1401 |
| BODIPY TR-X | 519.0 | 1110 |
| BODIPY 650/665 | 529.5 | 1107 |
| 5-Fluorescein (FITC) | 537.6 | 1000 |
| BODIPY 630/650 | 545.5 | 1113 |
| 3'6-Carboxyfluorescein (FAM) | 569.5 | 1007 |
| Cascade Blue | 580.0 | 1705 |
| Alexa Fluor 430 | 586.8 | 1731 |
| Lucifer Yellow | 605.5 | 1715 |
| WellRED D2-PA | 611.0 | 1600 |
| DY-555 | 636.2 | 1410 |
| WellRED D3-PA | 645.0 | 1601 |
| Rhodamine Red-X | 654.0 | 1302 |
| DY-782 | 660.9 | 1421 |
| DY-700 | 668.9 | 1417 |
| Alexa Fluor 568 | 676.8 | 1736 |
| 5(6)-Carboxyeosin | 689.0 | 3310 |
| Texas Red-X | 702.0 | 1301 |
| DY-675 | 706.9 | 1416 |
| DY-750 | 713.0 | 1420 |
| DY-681 | 736.9 | 1423 |
| 6-Hexachlorofluorescein (HEX) | 744.1 | 1005 |
| LightCycler Red 705 | 753.0 | 1011 |
| DY-636 | 760.9 | 1414 |
| DY-701 | 770.9 | 1424 |
| FAR-Fuchsia (5'-Amidite) | 776.0 | 1020 |
| DY-676 | 808.0 | 1422 |
| Erythrosin | 814.0 | 3311 |
| FAR-Blue (SE) | 824.0 | 1023 |
| Oyster 556 | 850.0 | 1800 |
| Oyster 656 | 900.0 | 1802 |
| Alexa Fluor 546 | 964.4 | 1734 |
| FAR-Green One (SE) | 976.0 | 1024 |
| Alexa Fluor 660 | 985.0 | 1740 |
| Oyster 645 | 1000.0 | 1801 |
| Alexa Fluor 680 | 1035.0 | 1741 |
| Alexa Fluor 633 | 1085.0 | 1738 |
| Alexa Fluor 555 | 1135.0 | 1735 |
| Alexa Fluor 750 | 1185.0 | 1743 |
| Alexa Fluor 700 | 1285.0 | 1742 |

TABLE 2

1,2-Diacyl-sn-Glycero-3-Phosphocholine Saturated Series (Symmetric Fatty Acid) (cited from Avanti Polar Lipid Catalog)

| Carbon Number | Trivial | IUPAC | M.W. | Catalog Number |
|---|---|---|---|---|
| 3:00 | Propionoyl | Trianoic | 369.4 | 850302 |
| 4:00 | Butanoyl | Tetranoic | 397.4 | 850303 |
| 5:00 | Pentanoyl | Pentanoic | 425.5 | 850304 |
| 6:00 | Caproyl | Hexanoic | 453.5 | 850305 |
| 7:00 | Heptanoyl | Heptanoic | 481.6 | 850306 |
| 8:00 | Capryloyl | Octanoic | 509.6 | 850315 |
| 9:00 | Nonanoyl | Nonanoic | 537.7 | 850320 |
| 10:00 | Capryl | Decanoic | 565.7 | 850325 |
| 11:00 | Undecanoyl | Undecanoic | 593.8 | 850330 |
| 12:00 | Lauroyl | Dodecanoic | 621.9 | 850335 |
| 13:00 | Tridecanoyl | Tridecanoic | 649.9 | 850340 |
| 14:00 | Myristoyl | Tetradecanoic | 678.0 | 850345 |
| 15:00 | Pentadecanoyl | Pentadecanoic | 706.0 | 850350 |
| 16:00 | Palmitoyl | Hexadecanoic | 734.1 | 850355 |
| 17:00 | Heptadecanoyl | Heptadecanoic | 762.2 | 850360 |
| 18:00 | Stearoyl | Octadecanoic | 790.2 | 850365 |
| 19:00 | Nonadecanoyl | Nonadecanoic | 818.2 | 850367 |
| 20:00 | Arachidoyl | Eicosanoic | 846.3 | 850368 |
| 21:00 | Heniecosanoyl | Heneicosanoic | 874.3 | 850370 |
| 22:00 | Behenoyl | Docosanoic | 902.4 | 850371 |
| 23:00 | Trucisanoyl | Trocosanoic | 930.4 | 850372 |
| 24:00 | Lignoceroyl | Tetracosanoic | 958.4 | 850373 |

The molecules of Tables 1 and 2 can be used as mass tags in the vesicle or vesicle components, respectively. If more probes are necessary, polynucleotides or peptides with different sequences can be utilized as mass tags or attached to mass tags because the combination of four nucleotides or twenty-one amino acids with different molecular mass can constitute hundreds of molecules with different molecular weights. This idea can be expanded to combinatorial chemistry, so hundreds, thousands, or millions of "mass tag" molecules can be prepared.

In some embodiments, the mass label may generally be any compound that may be detected by mass spectrometry. In particular embodiments, the mass label may be a biopolymer comprising monomer units, wherein each monomer unit is separately and independently selected from the group consisting essentially of an amino acid, a nucleic acid, and a saccharine with amino acids and nucleic acids being preferred monomer units. Because each monomer unit may be separately and independently selected, biopolymer mass labels may be polynucleic acids, peptides, peptide nucleic acids, oligonucleotides, and so on.

As defined herein "nucleic acids" refer to standard or naturally-occurring as well as modified/non-natural nucleic acids, often known as nucleic acid mimics. Thus, the term "nucleotides" refers to both naturally-occurring and modified/non-naturally-occurring nucleotides, including nucleoside tri-, di-, and monophosphates as well as monophosphate monomers present within polynucleic acid or oligonucleotide. A nucleotide may also be a ribo; 2'-deoxy; 2',3'-deoxy as well as a vast array of other nucleotide mimics that are well-known in the art. Mimics include chain-terminating nucleotides, such as 3'-O-methyl, halogenated base or sugar substitutions; alternative sugar structures including nonsugar, alkyl ring structures; alternative bases including inosine; deaza-modified; chi, and psi, linker-modified; mass label-modified; phosphodiester modifications or replacements including phosphorothioate, methylphosphonate, boranophosphate, amide, ester, ether; and a basic or complete internucleotide replacements, including cleavage linkages such a photocleavable nitrophenyl moieties. These modifications are well known by those of skill in the art and based on fundamental principles as described in Sanger (1983), incorporated herein by reference.

Similarly, the term "amino acid" refers to a naturally-occurring amino acid as well as any modified amino acid that may be synthesized or obtained by methods that are well known in the art.

In another embodiment, the mass label may be a synthetic polymer, such as polyethylene glycol, polyvinyl phenol, polypropylene glycol, polymethyl methacrylate, and derivatives thereof. Synthetic polymers may typically contain monomer units selected from the group consisting essentially of ethylene glycol, vinyl phenol, propylene glycol, methyl methacrylate, and derivatives thereof. More typically the mass label may be a polymer containing polyethylene glycol units. Alternatively, the amphiphilic molecules that make up the vesicle may themselves be used as mass tag molecules. For example, vesicles could be created from amphiphilic molecules having differing masses.

The mass label is typically detectable by a method of mass spectrometry. While it is envisioned that any known mass spectrometry method may be used to detect the mass labels of the present invention, methods such as matrix-assisted laser-desorption ionization mass spectrometry, direct laser-desorption ionization mass spectrometry (with no matrix), electrospray ionization mass spectrometry, secondary neutral mass spectrometry, and secondary ion mass spectrometry are preferred.

In certain embodiments the mass label has a molecular weight greater than, but not limited to, about 500 Daltons. For some embodiments, it may be preferred to have nonvolatile (including involatile) mass labels; however, for other embodiments volatile mass labels are also contemplated.

The probes of the present invention have advantages not only in multiplex capability, but also in sensitivity. According to the calculation shown in the Table 3, a 100-nm vesicle can retain 315 mass tag molecules in its inside, 62,800 molecules in its membrane, or 6,342,800 molecules in its membrane and inner vesicles. Moreover, these vesicles can preferably encapsulate more molecules by encapsulating their solid forms (powder, crystal, and other forms known to those skilled in the art) in S/O/W emulsion, soluble beads, soluble capsule. When a single detection probe retains more mass tag molecules, more sensitive detection can be accomplished. For example, Table 3 (below) indicates that a probe containing 6,342,800 mass tag molecules can increase the sensitivity $10^6 \sim 10^7$ times more than without the probe.

TABLE 3

| Diameter of Vesicle [nm] | "mass tag" molecules in a Vesicle [-] | | |
| --- | --- | --- | --- |
| | Encapsulated Vesicle (*1) | Uni-lamellar Vesicle (*2) | Multi-lamellar Vesicle (*3) |
| 1 | 0.00 | 6.28 | 634 |
| 10 | 0.32 | 628 | 63,428 |
| 100 | 315 | 62,800 | 6,342,800 |
| 500 | 39,381 | 1,570,000 | 158,570,000 |

(*1): Assuming that 1M "mass tag" molecules are encapsulated in vesicles.
(*2): Assuming that the vesicle membrane consists of 100% "mass tag" molecules and their density in the membrane is set as 0.5 nm$^2$/molecule (Faraday Discuss, 1998, 111, 79-94).
(*3): Assuming that the vesicle membrane consists of 100% "mass tag" molecules and the vesicle encapsulates 1,000,000 of 100-times smaller vesicles whose membrane also consists of 100% "mass tag" molecules.

In addition, in preferred embodiments reproducible detection can be achieved because the number of the mass tag molecules in a single probe can preferably be determined by the size of the vesicle, which can be controlled by size exclusion chromatography or membrane filtration. The size of these vesicles can be measured by several methods, including but not limited to: size exclusion chromatography, coulter counter, light scattering, centrifugation, electron microscopy and atomic force microscopy.

These probes can preferably be applied to simultaneously analyze multiple samples (different source, different time, different stimulation, sample duplication or others known to those skilled in the art) or multiple targets (different genes, proteins, small compounds, and other targets known to those skilled in the art).

When multiple samples are to be analyzed, detection of these interactions in accordance with a preferred embodiment of the present invention can preferably be performed by the following steps: label each sample with different probes, mix the labeled samples, allow interaction with a target molecule immobilized on a surface, wash and remove unbound samples, collect the mass tag molecules from the vesicle, and quantify the mass tag molecules.

When multiple targets are to be analyzed, detection in accordance with a preferred embodiment of the present invention can preferably be performed by the following steps: combine multiple target-tethered vesicle probes, allow interaction with a sample immobilized on a surface, wash and remove unbound probes, collect the mass tag molecules from the vesicle, and quantify the mass tag molecules.

To collect the mass tag molecules, physical stimulation (including, but not limited to heat, centrifugation, laser irradiation, sonication, electricity, and other methods known to those skilled in the art) and/or chemical stimulation (including, but not limited to addition of organic solvent, detergent, acid, alkaline, chaotropic reagents, change of buffer/salt concentration, pH, osmotic pressure, and other methods known to those skilled in the art) can preferably be used to disrupt the vesicles and collect the mass tag molecules for the following analysis. Also, to analyze the "mass tag" molecules, mass spectrometry, electrophoresis or chromatography can preferably by use to identify the molecular weight (or mobility) of each mass tag. In preferred embodiments, the concentration of mass tag molecules can be simultaneously quantified. Also, these vesicle probes may preferably carry other compound tags such as raman-active compounds, fluorescent dyes and luminescent dyes

EXAMPLES

Hybridization Assay

The above encapsulated, uni-lamellar, and multi-lamellar vesicle probes were tested using a hybridization assay.

Oligo(dA)$_{20}$ and oligo(dT)$_{20}$-tethered vesicles were prepared. The encapsulated and uni-lamellar vesicles were prepared in the following steps: 20 µmol of 1,2-dipalmitoyl-sn-glycero-3-phosphocholine (DPPC), 20 µmol of cholesterol, 2 µmol of 1,2-dipalmitoyl-sn-glycero-3-[phosphor-rac-(1-glycerol)] (DPPG) and 1 µmol of 1,2-dipalmitoyl-sn-glycero-3-phosphoethanolamine-N-(glutaryl) (glutaryl-DPPE) were dried off in chloroform under a vacuum. The dried lipids were swelled in 1 ml of 50 mM Tris-HCl, pH 7.4, 500 mM NaCl and 100 mM sulforhodamine B (SRB) at 45° C. for 1 hour. The vesicles were prepared by filtering the mixture thirty times with a 2.0-µm-pore membrane and thirty times with a 0.2-µm-pore membrane. The vesicles were purified from unincorporated SRB by G-25 column.

The multi-lamellar vesicle was prepared in several steps. For the "inside liposome," 10 µmol of 1,2-dipalmitoyl-sn-glycero-3-phosphocholine (DPPC), 10 µmol of cholesterol and 1.5 µmol of 1,2-dipalmitoyl-sn-glycero-3-[phosphor-rac-(1-glycerol)] (DPPG) were dried off in chloroform under a vacuum. The dried lipids were swelled in 0.5 ml of 50 mM Tris-HCl, pH 7.4, 500 mM NaCl at 45° C. for 1 hour. The "small vesicles" were prepared by sonication for 30 minutes at 45° C. The liposome encapsulated inside of the liposome was prepared by drying off 10 µmol of 1,2-dipalmitoyl-sn-glycero-3-phosphocholine (DPPC), 10 µmol of cholesterol, 1 µmol of 1,2-dipalmitoyl-sn-glycero-3-[phosphor-rac-(1-glycerol)] (DPPG) and 0.5 µmol of 1,2-dipalmitoyl-sn-glycero-3-phosphoethanolamine-N-(glutaryl) (glutaryl-DPPE) in chloroform under a vacuum. The dried lipids were swelled in 0.5 ml of the "inside liposome" solution (described above) at 45° C. for 1 hour. The mixture was filtered 30 times with a 2.0-µm-pore membrane and 30 times with a 0.2-µm-pore membrane.

Immobilization of oligonucleotide onto the vesicles was performed in the following steps: 1 nmol oligo$(dA)_{20}$ or oligo$(dT)_{20}$ was activated with thiol modification at its 5' end by incubation in 10 mM DTT for 15 min at 45° C. The activated oligonucleotide was purified by G-25 column. The oligonucleotide was mixed with 50 µl vesicle solution at room temperature overnight.

Figure 2:
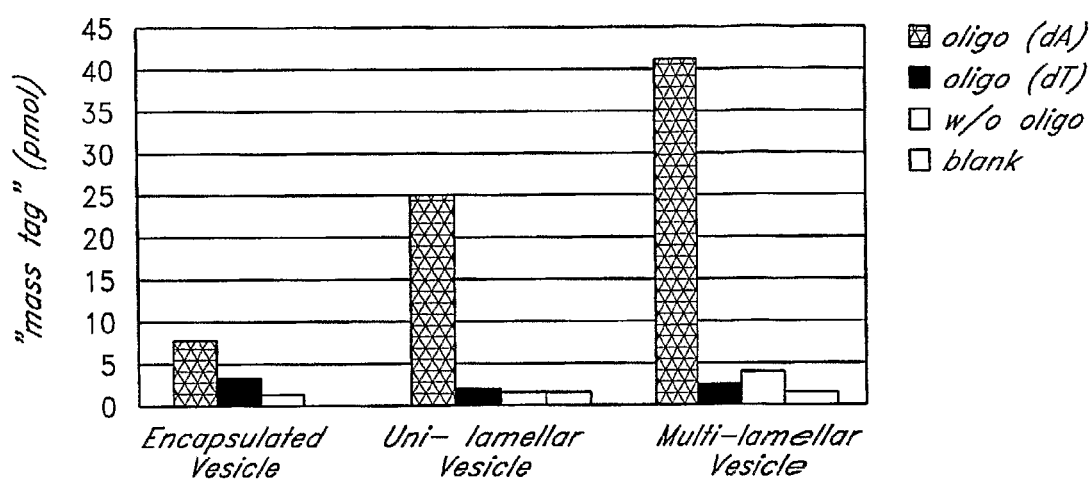
FIG. 2 is a graph showing hybridization assay results for various vesicle types.

The mass tag of the encapsulated vesicle was sulforhodamine B (SRB) encapsulated in the vesicles, and that of the uni- and multi-lamellar vesicle was 1,2-dipalmitoyl-sn-glycero-3-phosphocholine (DPPC) that accounts for approximately 50% of the membrane components. The vesicles in the hybridization buffer (10 mM Tris, pH 7.4, 500 mM NaCl) were incubated in an oligo$(dT)_{20}$-immobilized microplate (RNAture, CA) for 1 hour at room temperature. After three washes with the hybridization buffer, the hybridized vesicles on the well surfaces were disrupted by addition of 100% methanol. The mass tag molecules were collected into methanol and were analyzed by ESI-TOF mass spectrometry (Waters, Mass.), and quantified by the mass intensities of the corresponding mass peaks. As shown in FIG. 2, The results indicated that the vesicles with complemented oligo$(dA)_{20}$ were captured specifically in the oligo$(dT)_{20}$ microplate in comparison with those with non-complemented oligo$(dT)_{20}$ or without oligonucleotide. In FIG. 2, "Oligo(dA)" and "oligo(dT)" are the oligo$(dA)_{20}$- and oligo$(dT)_{20}$-tethered vesicles captured by the oligo$(dT)_{20}$-immobilized microplate, respectively. "W/o oligo" is the vesicle without oligonucleotide captured by the oligo$(dT)_{20}$ microplate, and "blank" is 100% methanol. In the encapsulated vesicle, the "mass tag" is sulforhodamine B and quantified by the mass peak at m/z=580.60. In the uni- and multi-lamellar vesicles, "mass tag" is DPPC and quantified by the mass peak at m/z=756.05.

Multiplex Microarray Assay

Figure 3:
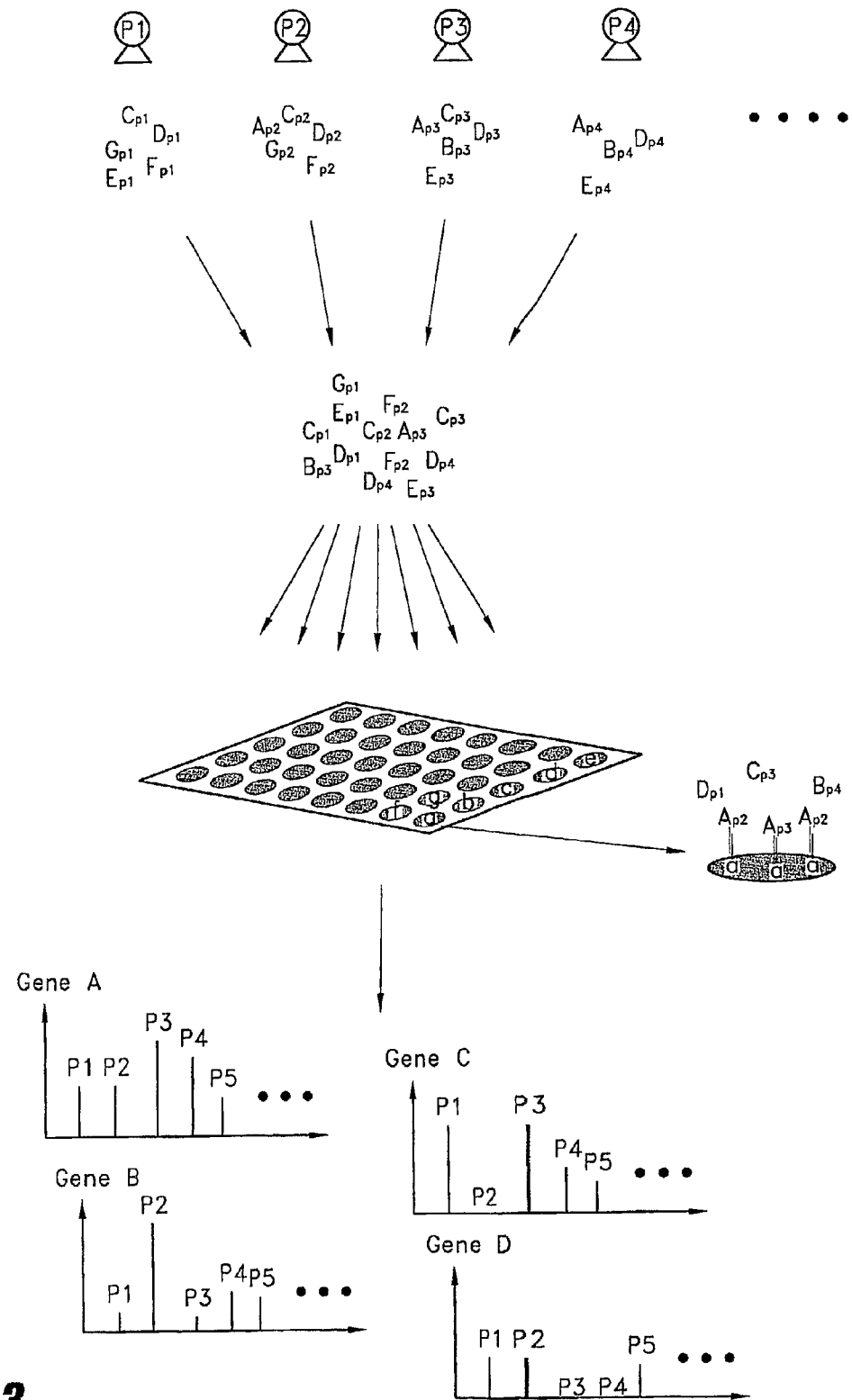
FIG. 3 is a schematic depiction of a multiplex microarray process with mass tag molecules.

The messenger RNA or their transcribed cDNA (gene A, B, C, etc.) from Sample P1, P2, P3, etc. of FIG. 3 are labeled with the mass tag probes (p1, p2, p3, etc., which correspond to P1, P2, P3, etc., respectively) to identify their respective sample sources. Labeling is accomplished by several methods such as chemical reaction with active residues on the probe, incorporation of the DNTP attached with the probes and cDNA synthesis using the oligo(dT) or specific sequence primer tethered on the probes. These labeled genes are combined together and applied to a surface with multiple spots where specific sequence polynucleotides (gene a, b, c, etc., which are complement with gene A, B, C, etc., respectively) are immobilized. After hybridization and several washes, each gene spot captures its respective complement gene from multiple samples. Laser irradiation onto each spot disrupts the probes on the spot and ionizes the mass tag molecules for mass spectrometry (MALDI, etc.). Alternatively, addition of organic solvent disrupts the probes and collects the mass tag molecules for mass spectrometry (ESI, etc.) or other analytical methods. The mass peaks of the mass tag molecules obtained from each gene spot simultaneously give the amounts of its complement gene expressed in different samples.

Multiplex Immunoassay

Figure 4:
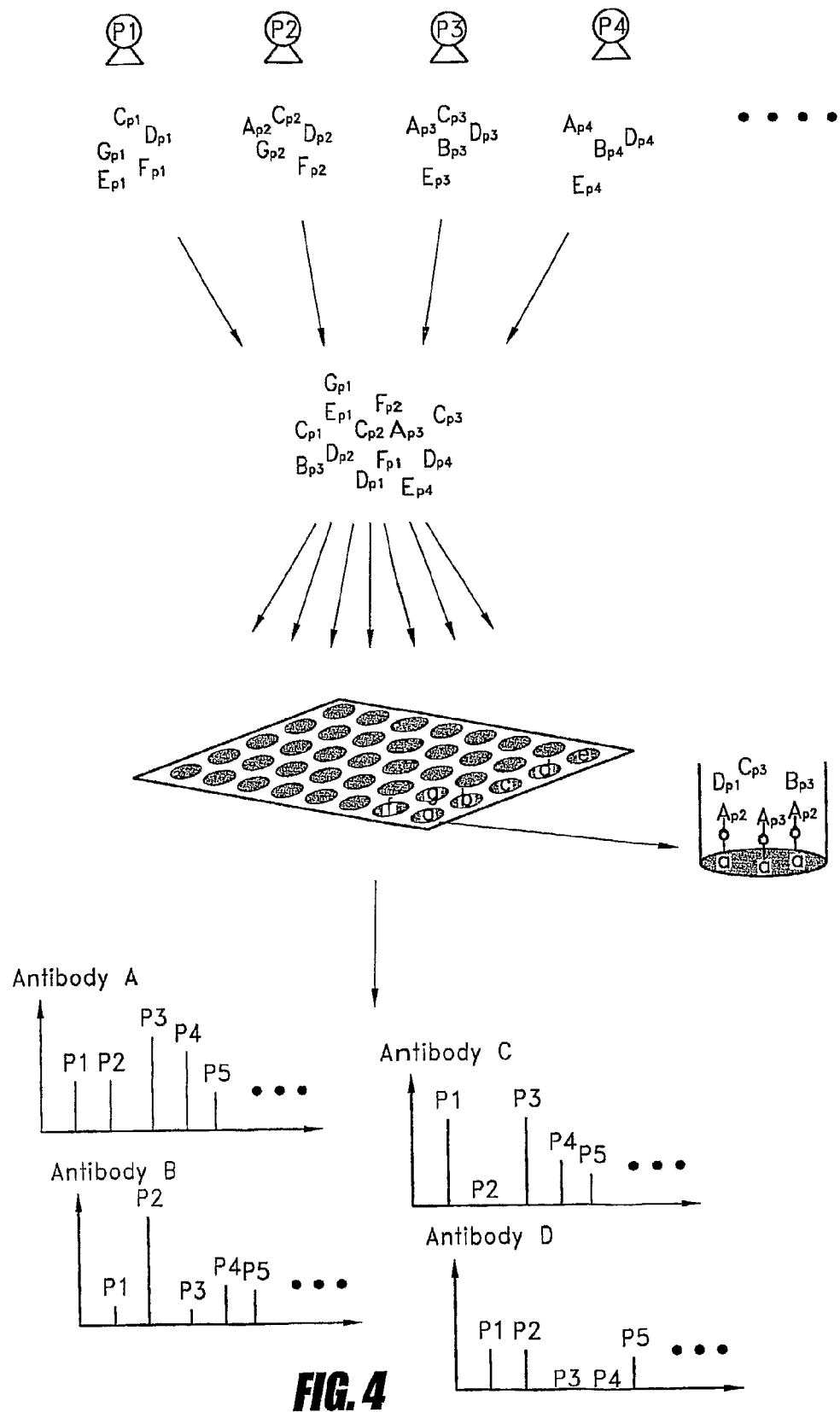
FIG. 4 is a schematic depiction of a multiplex immunoassay with mass tag molecules.

Antibodies (A, B, C, etc.) from sample P1, P2, P3, etc. of FIG. 4 are labeled with the mass tag probes (p1, p2, p3, etc., which corresponds to P1, P2, P3, etc., respectively). The labeled antibodies are combined together and applied to a microplate where each well has a different antigen (a, b, c, etc., which specifically bind to Antibody A, B, C, etc., respectively). After incubation and several washes, each well captures its respective antibody from multiple samples. Laser irradiation onto each well disrupts the probes on the spot and ionizes the mass tag molecules for mass spectrometry (MALDI, etc.) or addition of organic solvent disrupts the probes and collects the mass tag molecules for mass spectrometry (ESI, etc.). The mass peaks of the mass tag molecules obtained from each well simultaneously give the amounts of the corresponding antibody expressed in different samples.

Multiplex Hybridization Assay

Figure 5:
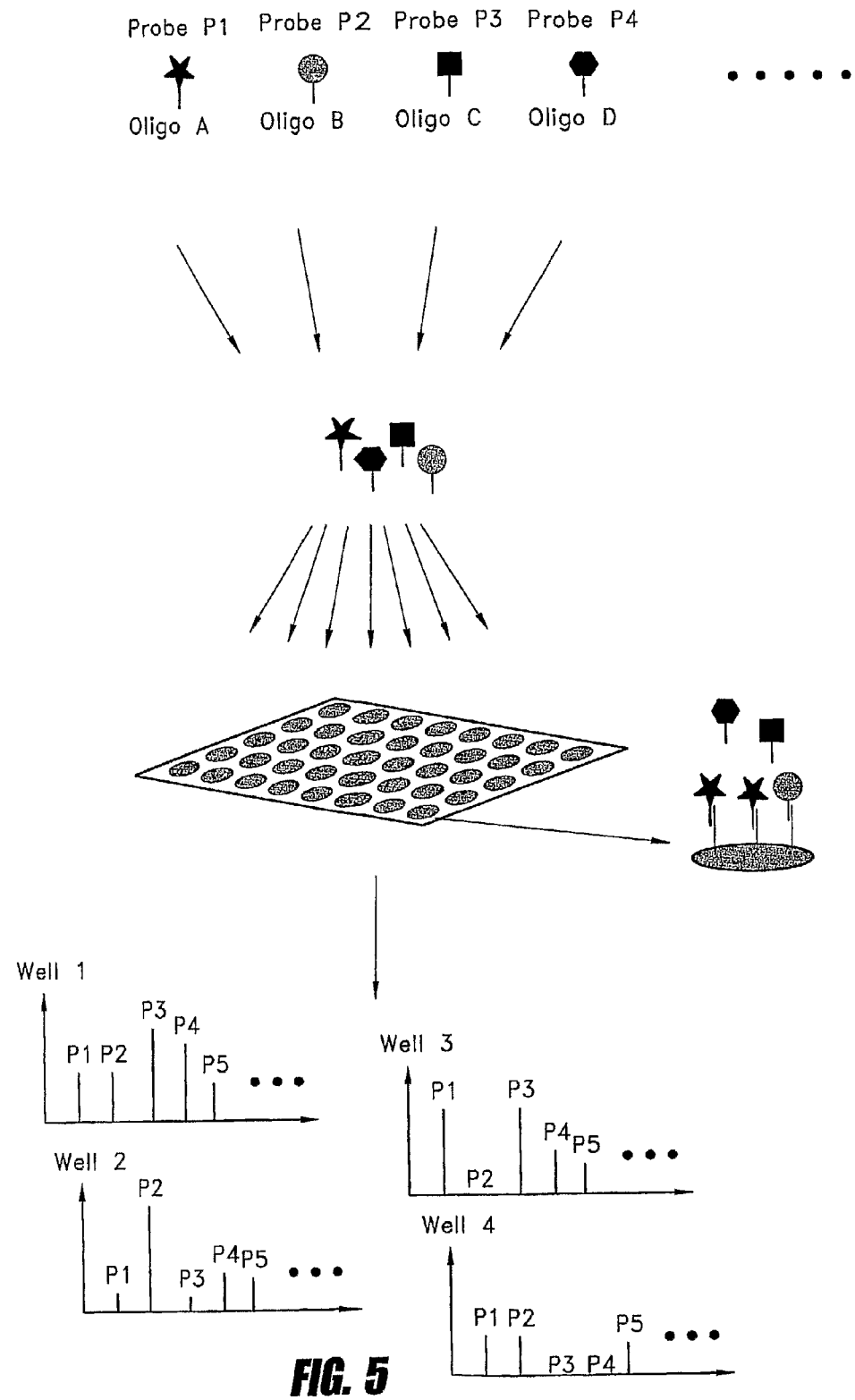
FIG. 5 is a schematic depiction of a multiplex hybridization with mass tag molecules.

Multiple hybridization probes (Probe P1, P2, P3, etc.) tethered with their corresponding sequence-specific oligonucleotides (Oligo A, B, C, etc., which are complement to target genes, Gene a, b, c, etc., respectively) are prepared, as illustrated in FIG. 5. These probes are combined together and applied to a sample DNA or RNA immobilized on a solid surface by hybridization (mRNA captured by oligo(dT)-coated surface, etc.), physical adsorption (DNA/RNA captured on a glass-fiber surface, etc.), synthesis (DNA/RNA synthesis by polymerase or chemical reaction, etc.) or other methods known to those skilled in the art. After hybridization and several washes, only the probes corresponding to the genes expressed in the sample are captured on the surface. Therefore, analyzing the concentrations of the mass tag molecules on the surface simultaneously gives the multiple gene profiles in the sample DNA/RNA.

Multiplex CpG Methylation Assay

Multiple oligonucleotide-tethered probes are prepared to hybridize against specific sequences of their corresponding CpG methylation sites on genomic DNA. These probes are combined together and applied to fragmented sample DNA captured on a surface coated with CpG-methyl-specific antibody or chemical residue. After incubation and several washes, only the probes corresponding to the CpG methyls expressed in the sample are captured on the surface. Therefore, analyzing the concentrations of the "mass tag" molecules on the surface gives the expression profiles of multiple CpG methylation sites in the sample simultaneously.

Capillary Assay

Figure 6:
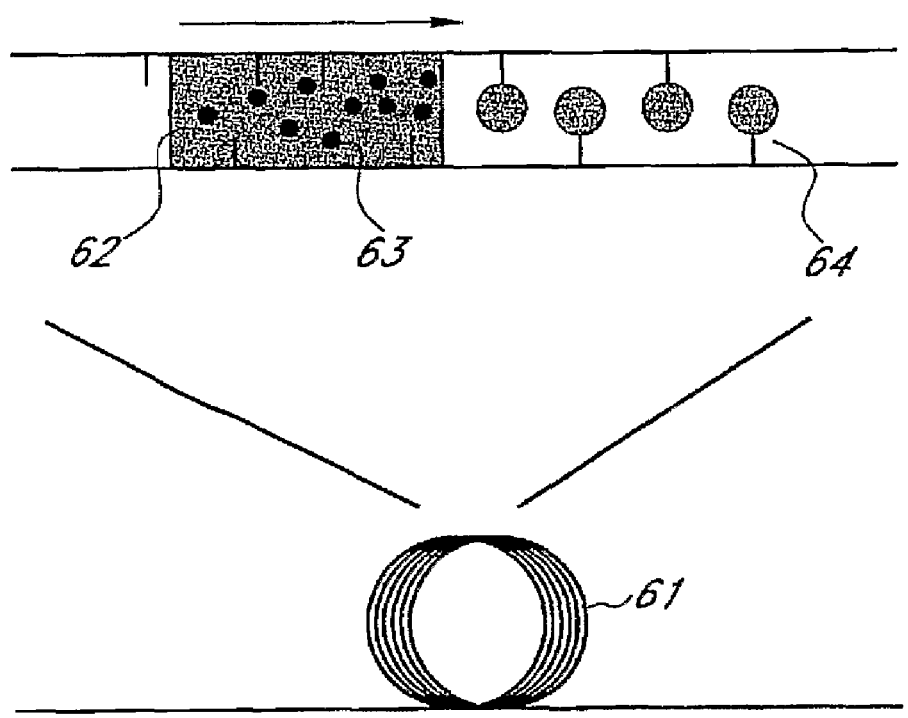
FIG. 6 is a schematic depiction of a capillary assay with mass tag molecules.

As illustrated in FIG. 6, biological samples (DNA, RNA, protein, small compound, etc.) labeled with the probes or target-specific probes (hybridization probe, antibody probe, etc.) are prepared, combined and applied to a capillary 61. On the inside wall of the capillary 61, specific target molecules or samples (DNA, RNA, protein, small compound, etc.) are immobilized. After incubation and several washes, specifically bound molecules are captured on the inside wall of the capillary by intermolecular interaction such as hybridization, protein-protein interaction or antigen-antibody interaction. A limited amount of organic solvent 62 disrupts the probe 64 on the wall and collects the "mass tag" molecules 63 in the limited volume when it passes through the capillary 61, therefore the collected "mass tag" molecules 63 are analyzed at higher concentration.

What is claimed is:

1. A detection probe comprising:
an external vesicle comprising a plurality of amphiphilic molecules forming a vesicle membrane;
a plurality of mass tag molecules encapsulated within the vesicle, within the vesicle membrane or adsorbed on the vesicle membrane; and
a probe attached to the vesicle.

2. The detection probe of claim 1, wherein the external vesicle is disruptible by physical or chemical stimulation to release the mass tag molecules.

3. The detection probe of claim 1, wherein the plurality of mass tag molecules comprise at least a part of the vesicle membrane.

4. The detection probe of claim 1, further comprising at least one vesicle encapsulated within the external vesicle, at least a part of the external and encapsulated vesicles comprising the mass tag molecules.

5. The detection probe of claim 4, wherein the external and encapsulated vesicles are disruptible by physical or chemical stimulation to release the mass tag molecule.

6. The detection probe of claim 1, wherein the probe comprises at least one molecule selected from the group consisting of chemical residues, polynucleotides, polypeptides, and carbohydrates.

7. The detection probe of claim 1, wherein the mass tag molecules are a biopolymer.

8. The detection probe of claim 1, wherein the mass tag molecules are polymers selected from the group consisting of block copolymers, polyethylene glycol, polyvinyl phenol, polyproplene glycol, polymethyl methacrylate, and derivatives thereof.

9. The detection probe of claim 1, wherein the mass tag molecules are an amphiphilic molecule bound to a polymer.

10. A method of analyzing a plurality of different biological samples, each of said samples comprising a plurality of analytes, said method comprising:
labeling each sample with a detection probe according to claim 1, wherein the mass tag molecules of the detection probe labeling each sample have a different mass;
incubating the labeled sample with an immobilized target molecule capable of specifically binding to one of said analytes;
removing unbound labeled sample;
collecting the mass tag molecules from the bound probe; and
quantifying the mass tag molecules collected.

11. The method of claim 10, wherein the binding of the detection probe results from the binding of molecules.

12. The method of claim 11, wherein the molecules are DNA, RNA, aptamers, proteins, peptides, polysaccharides or chemical residues on biological molecules.

13. The method of claim 10, wherein the mass tag molecules are collected after stimulation of the detection probes.

14. The method of claim 13, wherein the stimulation is a solvent change, chemical addition, pH change, agitation, sonication, heating, laser irradiation, light irradiation or freeze-thaw process.

15. The method of claim 10, wherein the quantification method is selected from the group consisting of mass spectrometry, electrophoresis and chromatography.

16. A detection probe, comprising:
a body comprising a material that becomes soluble in a solvent upon physical or chemical stimulation and at least one mass tag molecule, wherein the solvent is selected from the group consisting of water, buffer, acid, alkali, and organic solvent; and
a probe attached to the body.

17. The detection probe of claim 16, wherein the body comprises a bead.

18. The detection probe of claim 16, wherein the probe comprises at least one molecule selected from the group consisting of chemical residues, polynucleotides, polypeptides, and carbohydrates.

19. The detection probe of claim 16, wherein the mass tag molecule is a biopolymer.

20. The detection probe of claim 16, wherein the mass tag molecule is a polymer selected from the group consisting of a block copolymer, polyethylene glycol, polyvinyl phenol, polyproplene glycol, polymethyl methacrylate, and derivatives thereof.

21. A set of detection probes comprising:
a first detection probe comprising:
a first body comprising a material that becomes soluble in a solvent upon physical or chemical stimulation and at least one first mass tag molecule, wherein the solvent is selected from the group consisting of water, buffer, acid, alkali, and organic solvent; and
a first probe attached to the first body; and
a second detection probe comprising:
a second body comprising a material that becomes soluble in a solvent upon physical or chemical stimulation and at least one second mass tag molecule, wherein the solvent is selected from the group consisting of water, buffer, acid, alkali, and organic solvent; and
a second probe attached to the second body;
wherein the mass of the first mass tag molecule is different from the mass of the second mass tag molecule.

22. The set of detection probes of claim 21, wherein the first and second bodies comprise beads.

23. The set of detection probes of claim 21, wherein the first and second probes comprise at least one molecule selected from the group consisting of chemical residues, polynucleotides, polypeptides, and carbohydrates.

24. The set of detection probes of claim 21, wherein the first and second mass tag molecules are biopolymers.

25. The set of detection probes of claim 21, wherein the first and second mass tag molecules are synthetic polymers.

26. The set of detection probes of claim 21, wherein the first and second mass tag molecules are amphiphilic molecules bound to a biopolymer or synthetic polymer.

27. A set of detection probes comprising:
a first detection probe comprising:
a first external vesicle comprising a plurality of amphiphilic molecules forming a first vesicle membrane;
a plurality of first mass tag molecules encapsulated within the first external vesicle, within the first vesicle membrane or adsorbed on the first vesicle membrane; and
a probe attached to the first external vesicle; and
a second detection probe comprising:
a second external vesicle comprising a plurality of amphiphilic molecules forming a second vesicle membrane;
a plurality of second mass tag molecules encapsulated within the second external vesicle, within the second vesicle membrane or adsorbed on the second vesicle membrane; and a probe attached to the second external vesicle;

wherein the mass of the first mass tag molecules is different from the mass of the second mass tag molecules.

28. The set of detection probes of claim 27, wherein the first and second external vesicles are easily disrupted to release the mass tag molecule.

29. The set of detection probes of claim 27, wherein each of the first and second mass tag molecules is encapsulated within each of the first and second external vesicles, respectively.

30. The set of detection probes of claim 27, wherein each of the first and second mass tag molecules is encapsulated within each of the first and second vesicle membranes, respectively.

31. The set of detection probes of claim 27, wherein each of the first and second mass tag molecules is adsorbed on each of the first and second vesicle membranes, respectively.

32. The set of detection probes of claim 27, wherein the mass tag molecules comprise at least a part of the vesicle membranes.

33. The set of detection probes of claim 27, wherein each of the first and second external vesicles further comprise at least one encapsulated vesicle, at least a part of the external and encapsulated vesicles comprising the mass tag molecule.

34. The set of detection probes of claim 27, wherein the probes each comprise at least one molecule selected from the group consisting of chemical residues, polynucleotides, polypeptides, and carbohydrates.

35. The set of detection probes of claim 27, wherein the first and second mass tag molecules are biopolymers.

36. The set of detection probes of claim 27, wherein the first and second mass tag molecules are polymers selected from the group consisting of block copolymers, polyethylene glycol, polyvinyl phenol, polyproplene glycol, polymethyl methacrylate, and derivatives thereof.

37. The set of detection probes of claim 27, wherein the first and second mass tag molecules are amphiphilic molecules bound to a biopolymer or synthetic polymer.

38. A method of simultaneously assaying a plurality of different biological samples, each of said samples comprising a plurality of analytes, said method comprising:

immobilizing said analytes from each of said samples on a surface;

incubating said surface with the set of detection probes according to claim 27;

removing unbound detection probe;

collecting the first and second mass tag molecules from the bound detection probe; and quantifying the first and second mass tag molecules collected.

39. The method of claim 38, wherein the binding of the detection probe results from the binding of molecules.

40. The method of claim 39, wherein the molecules are DNA, RNA, aptamers, proteins, peptides, polysaccharides or chemical residues on biological molecules.

41. The method of claim 38, wherein the mass tag molecules are collected after stimulation of the detection probes.

42. The method of claim 41, wherein the stimulation is a solvent change, chemical addition, pH change, agitation, sonication, heating, laser irradiation, light irradiation or freeze-thaw process.

43. The method of claim 38, wherein the quantification method is selected from the group consisting of mass spectrometry, electrophoresis and chromatography.

* * * * *

UNITED STATES PATENT AND TRADEMARK OFFICE
CERTIFICATE OF CORRECTION

PATENT NO. : 7,595,155 B2  
APPLICATION NO. : 10/590832  
DATED : September 29, 2009  
INVENTOR(S) : Taku Murakami Page 1 of 1

It is certified that error appears in the above-identified patent and that said Letters Patent is hereby corrected as shown below:

At column 4, line 24, delete "polymerosomes," and insert --polymersomes,--, therefor.

At column 4, line 34, delete "a a" and insert --a--, therefor.

At column 9, line 33, delete "honnones," and insert --hormones,--, therefor.

At column 11, line 25, delete "Carboxynapthofluorescein" and insert --Carboxynaphthofluorescein--, therefor.

At column 12, line 23, delete "Heniecosanoyl" and insert --Heneicosanoyl--, therefor.

At column 12, line 24, delete "Trucisanoyl Trocosanoic" and insert --Tricosanoyl Tricosanoic--, therefor.

At column 12, line 44, delete "saccharine" and insert --saccharide--, therefor.

At column 14, line 43, delete "dyes" and insert --dyes.--, therefor.

At column 15, line 37, delete "FIG. 2, The" and insert --FIG. 2, the--, therefor.

At column 15, line 58, delete "DNTP" and insert --dNTP--, therefor.

At column 17, line 23, in Claim 8, delete "polyproplene" and insert --polypropylene--, therefor.

At column 17, line 57, in Claim 12, delete "polysaccharides" and insert --polysaccharides,--, therefor.

At column 18, line 19, in Claim 20, delete "polyproplene" and insert --polypropylene--, therefor.

At column 20, line 1, in Claim 36, delete "polyproplene" and insert --polypropylene--, therefor.

At column 20, line 21, in Claim 40, delete "polysaccharides" and insert --polysaccharides,--, therefor.

Signed and Sealed this

Twenty-seventh Day of April, 2010

David J. Kappos  
*Director of the United States Patent and Trademark Office*

UNITED STATES PATENT AND TRADEMARK OFFICE
CERTIFICATE OF CORRECTION

PATENT NO. : 7,595,155 B2  Page 1 of 1
APPLICATION NO. : 10/590832
DATED : September 29, 2009
INVENTOR(S) : Taku Murakami It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 448 days.

Signed and Sealed this

Twenty-eighth Day of September, 2010

David J. Kappos
*Director of the United States Patent and Trademark Office*